(12) United States Patent
Maimó et al.

(10) Patent No.: US 7,902,370 B2
(45) Date of Patent: Mar. 8, 2011

(54) SOLID FORMS OF THE MAGNESIUM SALT OF S-OMEPRAZOLE AND PROCESSES FOR THEIR PREPARATION

(75) Inventors: Ramón Berenguer Maimó, Barcelona (ES); Laura Coppi, Barcelona (ES); Yolanda Gasanz Guillén, Barcelona (ES); Jorge Medrano Rupérez, Barcelona (ES)

(73) Assignee: Esteve Quimica, S.A., Barcelona (ES)

( * ) Notice: Subject to any disclaimer, the term of this patent is extended or adjusted under 35 U.S.C. 154(b) by 1042 days.

(21) Appl. No.: 11/571,564

(22) PCT Filed: Jun. 29, 2005

(86) PCT No.: PCT/EP2005/053062
§ 371 (c)(1),
(2), (4) Date: Jan. 2, 2007

(87) PCT Pub. No.: WO2006/003163
PCT Pub. Date: Jan. 12, 2006

(65) Prior Publication Data
US 2007/0249684 A1 Oct. 25, 2007

(30) Foreign Application Priority Data
Jul. 2, 2004 (ES) .................................. 200401729

(51) Int. Cl.
*C07D 401/12* (2006.01)
(52) U.S. Cl. ..................................... 546/273.7
(58) Field of Classification Search ............... 546/273.7; 514/338
See application file for complete search history.

(56) References Cited

U.S. PATENT DOCUMENTS

| 5,900,424 | A | * | 5/1999 | Kallstrom et al. | ............ | 514/338 |
| 6,162,816 | A | * | 12/2000 | Bohlin et al. | ................. | 514/338 |
| 6,326,384 | B1 | | 12/2001 | Whittle et al. | | |
| 6,894,066 | B2 | * | 5/2005 | Sherman | ....................... | 514/338 |

FOREIGN PATENT DOCUMENTS

| EP | 1375497 A1 | 1/2004 |
| WO | WO 95/01977 A1 | 1/1995 |
| WO | WO 97/41114 A1 | 11/1997 |
| WO | WO 98/54171 A1 | 12/1998 |
| WO | WO 01/87831 A2 | 11/2001 |
| WO | WO 03/089408 A2 | 10/2003 |
| WO | WO/2004/020436 A1 | 3/2004 |
| WO | WO/2004/037253 A1 | 5/2004 |
| WO | WO/2004/089935 A1 | 10/2004 |

OTHER PUBLICATIONS

Nerurkar et al., Transport Processes in Pharmaceutical Systems, NY: Marcel Dekker, Inc., 2000, 575-611.*
Brittain ed., "Polymorphism in Pharmaceutical solids" NY: Marcel Dekker, Inc., 1999, pp. 1-2, 183-226.*
Cui, Ming-quan, et al., Research on the Synthesis of S-omeprozole Magnesium, Chinese Journal of Synthetic Chemistry, 2002, pp. 193-194, vol. 10, China Academic Journal Electronic Publishing House.
Cui, Ming-quan, et al., Research on the Synthesis of S-omeprozole Magnesium, Chinese Journal of Synthetic Chemistry, 2002, pp. 193-194, vol. 10, China Academic Journal Electronic Publishing House. Translation.

* cited by examiner

*Primary Examiner* — Patricia L Morris
(74) *Attorney, Agent, or Firm* — Peter B. Scull; Kristina M. Kalan; Berenbaum Weinshienk PC

(57) ABSTRACT

New solid forms of the active ingredient magnesium salt of S-omeprazole, obtainable by a preparation process including: a) crystallizing a magnesium salt of S-omeprazole from a solution of a magnesium salt of S-omeprazole in a solvent system that includes a mixture of methanol/water with an amount of water equal to or greater than about 0.01 ml/g of the magnesium salt of S-omeprazole starting material; b) isolating the magnesium salt of S-omeprazole that appears in the prior operation; c) separating the free organic solvent from the magnesium salt of S-omeprazole obtained or, alternatively, separating both the free solvent and the solvation solvent. The new solid forms are obtained by a reproducible and robust process, with high yield and elevated optical purity, which is useful for the preparation of pharmaceutical products that contain said active ingredient.

1 Claim, 1 Drawing Sheet

SOLID FORMS OF THE MAGNESIUM SALT OF S-OMEPRAZOLE AND PROCESSES FOR THEIR PREPARATION

The present invention relates to new solid forms of the magnesium salt of S-omeprazole and to processes for their preparation, as well as intermediates for their preparation.

BACKGROUND ART

The compound 5-methoxy-2-[[(4-methoxy-3,5-dimethyl-2-pyridinyl)methyl]sulfinyl]-1H-benzimidazole, which has the generic name omeprazole, was described for the first time in the document EP 5.129-A. Omeprazole is a sulphoxide that contains an asymmetric center in the sulphur atom, and therefore exists as a racemic mixture of two enantiomers, R-omeprazole and S-omeprazole. The R configuration corresponds to the (+)-enantiomer and the S configuration to the (−)-enantiomer.

Omeprazole is susceptible to degradation in acidic and neutral media. Its stability is also affected by other factors such as humidity, temperature and organic solvents. Certain salts of omeprazole are described in EP 124.495-A where it indicates that they are more stable during storage than the neutral form of omeprazole.

Omeprazole and its alkaline salts are effective inhibitors of gastric acid secretion and, therefore, are useful for the prevention and treatment of gastric acid-related disorders and inflammatory gastrointestinal diseases (e.g., gastric ulcer, duodenal ulcer, reflux esophagitis and gastritis). In addition, they can also be used for the treatment of other gastrointestinal disorders where a cytoprotectant and/or anti-gastric secretion effect is desired (e.g., in patients with gastrinomas, in patients with acute upper gastrointestinal hemorrhage, and in patients with a history of chronic and excessive alcohol consumption).

EP 652.872-A describes the magnesium salt of S-omeprazole, the formula of which is included below, and indicates that it possesses pharmacokinetic and metabolic properties that give it an improved therapeutic profile. There are other documents that describe different solid forms of magnesium salt of S-omeprazole. EP 984.957-A describes a trihydrate form of magnesium salt of S-omeprazole. WO 04/20436 describes a hydrate of magnesium salt of S-omeprazole in amorphous solid form. Finally, EP 1.375.497-A describes a magnesium salt of S-omeprazole with a grade of crystallinity of less than 67% and a magnesium salt of S-omeprazole with an amount of organic solvent of less than 7%.

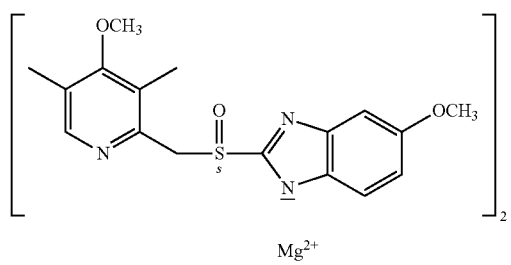

The different solid forms of a pharmaceutically active ingredient can have different characteristics, and offer certain advantages, for example with regard to solubility or bioavailability. Thus, the discovery of new solid forms allows for improving the characteristics of the pharmaceutical formulations of the active ingredients, since some forms are more adequate for one type of formulation, and other forms for other different formulations. Furthermore, depending on the therapeutic indications, one or another pharmaceutical formulation may be preferred, hence omeprazole may be commercialized, for example, in the form of capsules and vials, and S-omeprazole as gastroresistant tablets. It may hence be of interest to have new solid forms of magnesium salt of S-omeprazole.

SUMMARY OF THE INVENTION

According to one aspect of the present invention, a solid form of magnesium salt of S-omeprazole that gives the X-ray diffractogram shown in FIG. 1 may be provided. Said diffractogram differs from those of other forms of magnesium salt of S-omeprazole known in the state of the art. This new solid form of magnesium salt of S-omeprazole is characterized by exhibiting in the powder X-ray diffractogram a pattern of peaks, expressed in 2 theta units in degrees, 2θ (°), which is shown in the following table:

| 2θ (°) | d (Å) | Intensity (%) |
|--------|-------|---------------|
| 5.9    | 15.1  | 100           |
| 6.5    | 13.6  | 81            |
| 7.6    | 11.7  | 90            |
| 8.2    | 10.8  | 40            |

This form is essentially free of organic solvent, whether it be free or of solvation. The expression "essentially free of organic solvent" means that this form complies with the relevant pharmaceutical specifications for the presence of solvents. "Free of solvent" means that solvent does not form part of the product's crystalline structure, and solvation solvent means that solvent is incorporated into the crystalline structure of the same.

An X-ray diffractogram may be obtained using a Debye-Scherrer INEL CPS120 geometry diffractometer at a Cu—Kα1 radiation (λ=1.5406 Å) and at a power of 40 kV–30 mA.

A second aspect of the present invention relates to a process for the preparation of the magnesium salt of S-omeprazole, essentially free of organic solvent, that may comprise the following steps: a) crystallizing a magnesium salt of S-omeprazole from a solution of magnesium salt of S-omeprazole in a solvent system that comprises a mixture of methanol/water with an amount of water equal to or greater than about 0.01 ml/g of the magnesium salt of S-omeprazole starting material; b) isolating the magnesium salt of S-omeprazole that appears in the previous step; and c) separating the solvent from the magnesium salt of S-omeprazole obtained.

Preferably, the amount of water of the solvent system may be between about 0.01 and about 4 ml/g of the magnesium salt of the S-omeprazole starting material. It may be more preferable that the amount of water be between about 0.01 and about 2 ml/g of the magnesium salt of the S-omeprazole starting material. Even more preferable may be that the amount of water of the solvent system be between about 0.01 and about 0.5 ml/g of the magnesium salt of the S-omeprazole starting material. Even more preferable may be that the amount of water of the solvent system be between about 0.01 and about 0.1 ml/g of the magnesium salt of S-omeprazole starting material. The amount of water varies according to the dilution of the solution of the magnesium salt of S-omeprazole in the solvent system used and according to the solvents that form part of said solvent system, and can be added at the beginning or once the crystallization of the product has begun. This last possibility may be preferably used when the amounts of water are in the upper range, preferably from about 2 ml/g and up of magnesium salt of S-omeprazole.

The isolation of the product can be done by a conventional method such as filtration. In a preferred embodiment the separation of the solvent may be done by suspension of the magnesium salt of S-omeprazole in water, followed by isolation of the magnesium salt of S-omeprazole obtained and subsequent drying. In general, the suspension of the magnesium salt in water may be performed at a temperature between about 2° C. and about 30° C. and for about 30 to about 60 minutes. At higher temperatures the suspension time may be less. In another preferred embodiment the separation of the solvent may be done by drying at a temperature between about 60° C. and about 120° C.

In one particular embodiment of this preparation process, a cosolvent selected from $(C_1-C_4)$-alkyl esters and acetonitrile may be added to the solution of the magnesium salt of S-omeprazole in methanol/water. Preferably, the cosolvent may be selected from ethyl acetate or acetonitrile.

The magnesium salt of S-omeprazole of the present invention, essentially free of organic solvent, can also be obtained from a methanol-solvated magnesium salt of S-omeprazole, through a process of desolvation. A preferred methanol-solvated magnesium salt of S-omeprazole exhibits a pattern of peaks in the X-ray diffractogram, expressed in 2 theta units in degrees, 2θ (°), which is shown in the following table:

| 2θ (°) | d (Å) | Intensity (%) |
|---|---|---|
| 5.6 | 15.9 | 69 |
| 6.5 | 13.7 | 61 |
| 7.3 | 12.1 | 100 |
| 8.0 | 11.1 | 15 |
| 10.6 | 8.4 | 10 |
| 10.8 | 8.2 | 11 |
| 11.3 | 7.9 | 13 |
| 12.6 | 7.0 | 21 |
| 13.3 | 6.7 | 10 |
| 13.8 | 6.4 | 15 |
| 14.7 | 6.0 | 13 |
| 15.3 | 5.8 | 10 |
| 16.4 | 5.4 | 13 |
| 16.8 | 5.3 | 21 |
| 17.5 | 5.1 | 26 |
| 17.8 | 5.0 | 14 |
| 18.3 | 4.9 | 14 |
| 18.8 | 4.7 | 15 |
| 19.1 | 4.7 | 23 |
| 19.6 | 4.5 | 23 |
| 20.1 | 4.4 | 18 |
| 20.4 | 4.4 | 26 |
| 21.7 | 4.1 | 12 |
| 21.9 | 4.1 | 13 |
| 22.1 | 4.0 | 14 |
| 23.4 | 3.8 | 16 |
| 24.2 | 3.7 | 16 |
| 24.8 | 3.6 | 16 |
| 25.2 | 3.5 | 15 |
| 25.3 | 3.5 | 15 |
| 26.2 | 3.4 | 11 |
| 27.1 | 3.3 | 12 |
| 28.3 | 3.2 | 9 |
| 29.1 | 3.1 | 9 |
| 29.3 | 3.1 | 10 |
| 31.7 | 2.8 | 10 |

In a preferred embodiment, the desolvation process may be carried out by suspension in water, generally at a temperature between about 2° C. and about 30° C. for about 30 to about 60 minutes, followed by isolation of the obtained magnesium salt of S-omeprazole and by subsequent drying. In another preferred embodiment the desolvation process may be performed by drying at a temperature between about 60° C. and about 120° C.

This methanol-solvated magnesium salt of S-omeprazole that acts as an intermediate for the preparation of the solid form, essentially free of organic solvent of the present invention, can be prepared by a process which may comprise the following operations: a) crystallizing said magnesium salt of S-omeprazole from a solution of a magnesium salt of S-omeprazole in a solvent system that comprises a mixture of methanol/water with an amount of water that may be equal to or greater than about 0.01 ml/g of the magnesium salt of S-omeprazole starting material; b) isolating the magnesium salt of S-omeprazole obtained in the first operation; and c) drying the obtained magnesium salt of S-omeprazole at a temperature less than about 60° C. The drying temperature may preferably be about room temperature.

Preferably, the amount of water of the solvent system may be between about 0.01 and about 4 ml/g of the magnesium salt of S-omeprazole starting material. It may be preferable that the amount of water be between about 0.01 and about 2 ml/g of the magnesium salt of the S-omeprazole starting material. Even more preferable may be that the amount of water of the solvent system be between about 0.01 and 0.5 ml/g of the magnesium salt of the S-omeprazole starting material. Even more preferable may be that the amount of water of the solvent system may be between about 0.01 and about 0.1 ml/g of the magnesium salt of the S-omeprazole starting material. The amount of water may vary according to the dilution of the solution of the magnesium salt of S-omeprazole in the solvent system used and according to the solvents that form part of said solvent system, and can be added at the beginning or once the crystallization of the product has begun. This last possibility may preferably be used when the amounts of water are in the upper range, preferably from about 2 ml/g and up of a magnesium salt of S-omeprazole.

In one particular embodiment of this preparation process, a cosolvent selected from the group consisting of $(C_1-C_4)$-alkyl esters and acetonitrile may be added to the solution of the magnesium salt of S-omeprazole in methanol/water. Preferably, the cosolvent may be selected from ethyl acetate or acetonitrile.

The most adequate conditions for carrying out said processes vary depending on the parameters considered by the expert in the art, such as, for example, the concentration of the starting material, temperature, the cosolvent used, and the like. These can be easily determined by said skilled person in the art by routine tests and with the help of the teachings of the examples given in this description.

According to an additional aspect of the present invention, a preparation process may be provided that may allow for the obtaining of solid forms of the magnesium salt of S-omeprazole that comprises the following operations: a) crystallizing a magnesium salt of S-omeprazole from a solution of a magnesium salt of S-omeprazole in a solvent system that comprises a mixture of methanol/water with an amount of water that may be equal to or greater than about 0.01 ml/g of the magnesium salt of S-omeprazole starting material; b) isolating the magnesium salt of S-omeprazole that appears in the prior operation; and c) separating the organic solvent from the obtained magnesium salt of S-omeprazole. Therefore, the present invention may also include any solid form of magnesium salt of S-omeprazole obtainable by this preparation process.

Another aspect of the present invention relates to a pharmaceutical composition that may comprise as the active ingredient a therapeutically effective amount of the magnesium salt of S-omeprazole of the present invention, essentially free of organic solvent, together with suitable pharmaceutically acceptable excipients or carriers.

An advantage of the solid forms of the present invention may be that they have a high stability and physico-mechanical properties that allow for good manipulation for the preparation of solid pharmaceutical formulations. Another advantage of the solid forms of the present invention lies in the fact that they are obtained with high yields and elevated richness, that is, with a greater than about 99% purity and with levels of sulphone and N-oxide sulphone-common impurities in the synthesis of prazoles that are difficult to eliminate-significantly inferior to the beginning levels, staying below about 0.10%. Likewise, they are obtained with an elevated optical purity, that is, with an enantiomeric excess (e.e.) equal to or greater than about 99%, even when the starting material may be an optically contaminated magnesium salt of S-omeprazole. Furthermore, the solid forms of the present invention may have another additional advantage, given that their preparation process may be reproducible and robust, and, therefore, may be easily industrializable.

Throughout the description and the claims the word "comprises" and its variants are not meant to exclude other technical characteristics, additives, components, operations or steps. The summary of this application is included here for reference. For persons skilled in the art, other objects, advantages and characteristics of the invention can be deduced in part from the description and partly from the practice of the invention. The following examples are provided for illustrative means, and are not meant to be limiting of the present invention.

EXAMPLES

Example 1

Figure 1:
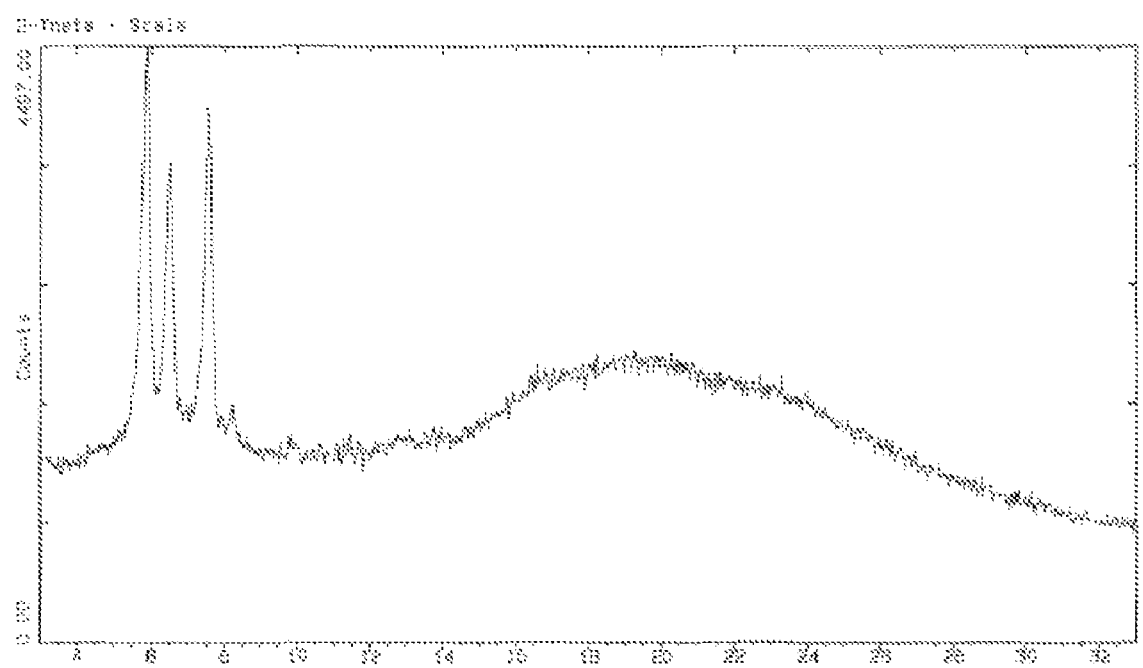
FIG. 1 shows the X-ray diffraction spectrum of the magnesium salt of S-omeprazole of the present invention, essentially free of organic solvent.

Preparation of a New Solid Form of the Methanol-Solvated Magnesium Salt of S-omeprazole About 20 g of magnesium salt of S-omeprazole (about 90.6% ee; Karl-Fischer: about 2.3%) were dissolved in about 60 ml of methanol at room temperature. About 300 ml of acetonitrile were added. The solid in suspension was filtered and dried at room temperature and at reduced pressure. About 17 g of the title compound were obtained (about 85% of yield; about 99.3% ee; about 4.3% p/p of methanol by gas chromatography).

Example 2

Preparation of a New Solid Form of Magnesium Salt of S-Omeprazole, Essentially Free of Organic Solvent About 5.0 g of the magnesium salt of S-omeprazole obtained in Example 1 were dried at about 70° C. and at reduced pressure, and about 4.9 g of the title compound were obtained. The X-ray diffraction analysis gave the diffractogram shown in FIG. 1.

Example 3

Preparation of a New Solid Form of the Magnesium Salt of S-Omeprazole, Essentially Free of Organic Solvent About 10.0 g of the magnesium salt of S-omeprazole, obtained according to Example 1 from a magnesium salt of S-omeprazole of a richness of about 97.7% a/a (N-oxide sulphone impurity: about 0.6% a/a and sulphone impurity: about 0.4% a/a), were suspended in about 50 ml of water. It was left stirring for about 45 minutes at room temperature and then the solid in suspension was filtered. It was dried at about 50° C. and at reduced pressure. About 9.5 g of the title compound were obtained (about 95% of yield; richness: about 99.7% a/a, N-oxide sulphone impurity: about 0.02% a/a; sulphone impurity: about 0.05% a/a). The X-ray diffraction analysis gave a diffractogram approximately equal to the one shown in FIG. 1.

Example 4

Preparation of a New Solid Form of the Magnesium Salt of S-Omeprazole, Essentially Free of Organic Solvent About 15.0 g of a magnesium salt of S-omeprazole (about 90.6% ee; Karl-Fischer: about 9.2%) were dissolved in about 45 ml of methanol at room temperature. About 270 ml of ethyl acetate were added. It was left stirring until the appearance of a solid in suspension. The solid was filtered and dried at about 90° C. and at reduced pressure. About 12.8 g of magnesium salt of S-omeprazole (about 85% of yield, about 99.2% ee) were obtained, which gives an X-ray diffractogram approximately equal to that shown in FIG. 1.

Example 5

Preparation of a New Solid Form of the Magnesium Salt of S-Omeprazole, Essentially Free of Organic Solvent About 2.0 g of the magnesium salt of S-omeprazole (Karl-Fischer: about 2.3%) were dissolved in about 6 ml of methanol. It was left stirring until the appearance of a solid in suspension. It was filtered, and dried at about 70° C. and at reduced pressure. About 1.2 g of magnesium salt of S-omeprazole (about 60% of yield) were obtained, which gives an X-ray diffractogram approximately equal to that shown in FIG. 1.

Example 6

Preparation of a New Solid Form of the Magnesium Salt of S-Omeprazole, Essentially Free of Organic Solvent About 20.0 g of the magnesium salt of S-omeprazole (Karl-Fischer: about 9.7%) were dissolved in about 100 ml of methanol. About 300 ml of acetonitrile and about 40 ml of water were added. The solid in suspension was filtered and dried at about 70° C. and reduced pressure. About 12.7 g of magnesium salt of S-omeprazole (about 64% of yield) were obtained, which gives an X-ray diffractogram approximately equal to that shown in FIG. 1.

The invention claimed is:
1. A solid form of the magnesium salt of enantiomer S-omeprazole having a crystalline structure and an X-ray diffractogram comprising characteristic peaks of greatest intensity at approximately 5.9, 6.5, and 7.6 degrees 2 theta, without any other significant peak.

* * * * *